United States Patent
Bullington et al.

(10) Patent No.: US 11,322,247 B2
(45) Date of Patent: *May 3, 2022

(54) MEDICAL APPOINTMENT PROGRESS TRACKING

(71) Applicants: Deborah T. Bullington, Jackson, WY (US); Andrew B. Bullington, Jackson, WY (US)

(72) Inventors: Deborah T. Bullington, Jackson, WY (US); Andrew B. Bullington, Jackson, WY (US)

(*) Notice: Subject to any disclaimer, the term of this patent is extended or adjusted under 35 U.S.C. 154(b) by 1028 days.

This patent is subject to a terminal disclaimer.

(21) Appl. No.: 14/794,857

(22) Filed: Jul. 9, 2015

(65) Prior Publication Data
US 2018/0150603 A1 May 31, 2018

(51) Int. Cl.
*G16H 40/20* (2018.01)
*G16H 10/60* (2018.01)

(52) U.S. Cl.
CPC .............. *G16H 40/20* (2018.01); *G16H 10/60* (2018.01)

(58) Field of Classification Search
CPC .................. G06Q 50/22; G06Q 50/24
See application file for complete search history.

(56) References Cited

U.S. PATENT DOCUMENTS

| 8,972,272 | B1* | 3/2015 | Dvorak | G16H 10/60 |
| | | | | 705/3 |
| 9,003,328 | B1 | 4/2015 | Boutcher et al. | |
| 10,134,488 | B1 | 11/2018 | Bullington et al. | |
| 10,741,279 | B2 | 8/2020 | Bullington et al. | |
| 10,796,795 | B1 | 10/2020 | Bullington et al. | |
| 2005/0234741 | A1 | 10/2005 | Rana et al. | |
| 2006/0184943 | A1 | 8/2006 | DelMonego et al. | |

(Continued)

FOREIGN PATENT DOCUMENTS

KR    20020070956 A  *  9/2002
WO       2017008064 A1     1/2017

OTHER PUBLICATIONS

S. Sankarananrayanan and S. M. A. Wani, "NFC enabled intelligent hospital appointment and medication scheduling," 2014 2nd International Conference on Information and Communication Technology (ICoICT), 2014, pp. 24-29, doi: 10.1109/ICoICT.2014.6914034. (Year: 2014).*

(Continued)

*Primary Examiner* — Lena Najarian
(74) *Attorney, Agent, or Firm* — Kwan & Olynick LLP

(57) ABSTRACT

Provided are mechanisms and processes for medical appointment progress tracking. According to various examples, the system includes a location sensor that tracks when a medical professional begins an examination of a patient by detecting when the medical professional logs into a computer to access the first patient's medical file. The system also includes a medical schedule processor that logs this time and compares this time with scheduling information to predict whether future appointments on that day will be delayed. The scheduling information is cryptographically separated from Health Insurance Portability and Accountability Act (HIPAA) information. The system further includes a notification interface that notifies upcoming patients if their appointments will be substantially delayed.

20 Claims, 7 Drawing Sheets

(56) References Cited

U.S. PATENT DOCUMENTS

| | | | | |
|---|---|---|---|---|
| 2006/0288095 | A1* | 12/2006 | Torok | G06Q 10/08 709/223 |
| 2007/0136118 | A1 | 6/2007 | Gerlach et al. | |
| 2007/0282654 | A1* | 12/2007 | Sarkar | G06Q 10/063116 705/7.16 |
| 2007/0294112 | A1 | 12/2007 | Settimi | |
| 2008/0195312 | A1 | 8/2008 | Aaron et al. | |
| 2009/0048865 | A1 | 2/2009 | Breazeale, Jr. | |
| 2009/0182576 | A1 | 7/2009 | Warner et al. | |
| 2009/0281825 | A1* | 11/2009 | Larsen | G06Q 10/10 705/2 |
| 2010/0042441 | A1 | 2/2010 | Steusloff et al. | |
| 2010/0094678 | A1 | 4/2010 | Gupta et al. | |
| 2010/0123560 | A1 | 5/2010 | Nix et al. | |
| 2010/0161345 | A1* | 6/2010 | Cain | G06Q 10/08 705/2 |
| 2010/0324922 | A1 | 12/2010 | Kendall et al. | |
| 2012/0065987 | A1 | 3/2012 | Farooq et al. | |
| 2013/0304534 | A1 | 11/2013 | Mehta et al. | |
| 2014/0278534 | A1 | 9/2014 | Romeo | |
| 2014/0278679 | A1 | 9/2014 | Navani et al. | |
| 2015/0170105 | A1 | 6/2015 | Lim | |
| 2015/0213414 | A1 | 7/2015 | Zuckerman et al. | |
| 2015/0223890 | A1 | 8/2015 | Miller et al. | |
| 2015/0242585 | A1 | 8/2015 | Spiegel | |
| 2017/0008064 | A1 | 1/2017 | Clare et al. | |
| 2018/0150602 | A1 | 5/2018 | Bullington et al. | |
| 2019/0051406 | A1 | 2/2019 | Bullington et al. | |
| 2020/0251208 | A1 | 8/2020 | Bullington et al. | |

OTHER PUBLICATIONS

"U.S. Appl. No. 14/794,851, Non Final Office Action dated Apr. 9, 2018", 12 pages.

"Int'l Application Serial No. PCT/US16/41657, Int'l Preliminary Report on Patentability", 8 pages.

"International Application Serial No. PCT/US16/41657, International Search Report and Written Opinion dated Sep. 22, 2016", 9 pages.

"U.S. Appl. No. 14/794,851, Notice of Allowance dated Aug. 29, 2018", 5 pages.

"U.S. Appl. No. 14/794,854, Non Final Office Action dated Jun. 15, 2018", 15 pages.

"U.S. Appl. No. 14/794,852, Non Final Office Action dated Jan. 22, 2019", 20 pgs.

"U.S. Appl. No. 14/794,854, Final Office Action dated Mar. 8, 2019", 16 pgs.

"U.S. Appl. No. 14/794,852, Examiner Interview Summary dated Apr. 16, 2019", 3 pages.

"U.S. Appl. No. 14/794,854, Examiner Interview Summary dated Jul. 9, 2019", 3 pgs.

U.S. Appl. No. 14/794,852, Non-Final Rejection, dated Feb. 21, 2020, 26 pgs.

U.S. Appl. No. 14/794,854, Non-Final Rejection, dated Jan. 15, 2020, 5 pgs.

U.S. Appl. No. 15/333,087, USPTO e-Office Action: CTNF—Non-Final Rejection, dated Mar. 20, 2020, 19 pgs.

U.S. Appl. No. 16/151,148, Non-Final Rejection, dated Feb. 6, 2020, 5 pgs.

U.S. Appl. No. 14/794,851, Non Final Office Action dated Apr. 9, 2018. 12 pgs.

U.S. Appl. No. 14/794,851, Notice of Allowance dated Aug. 29, 2018. 5 pgs.

U.S. Appl. No. 14/794,852, Examiner Interview Summary dated Apr. 16, 2019, 3pgs.

U.S. Appl. No. 14/794,854, Examiner Interview Summary dated Jul. 9, 2019, 3pts.

U.S. Appl. No. 14/794,852, Examiner Interview Summary Record (Ptol-413), dated Oct. 22, 2019, 2 pages.

International Application Serial No. PCT/US16/41657, International Search Report and Written Opinion dated Sep. 22, 2016. 9 pgs.

Int'l Application Serial No. PCT/US16/41657, Int'l Preliminary Report on Patentability. 8 pgs.

U.S. Appl. No. 14/794,852, Final Rejection, dated Aug. 7, 2020, 17 pgs.

U.S. Appl. No. 14/794,852, Examiner Interview Summary Record (Ptol-413), dated May 22, 2020, 2 pgs.

U.S. Appl. No. 14/794,854, Notice Of Allowance And Fees Due (Ptol-85), dated Jun. 8, 2020, 7 pgs.

U.S. Appl. No. 15/333,087, Office Action Appendix, dated Jun. 23, 2020, 2 pgs.

U.S. Appl. No. 15/333,087, Notice Of Allowance And Fees Due (Ptol-85), dated Jul. 30, 2020, 8 pgs.

U.S. Appl. No. 15/333,087, Notice Of Allowance And Fees Due (Ptol-85), dated Sep. 10, 2020, 5 pgs.

U.S. Appl. No. 16/151,148, Notice Of Allowance And Fees Due (Ptol-85), dated May 29, 2020, 5 pgs.

\* cited by examiner

MEDICAL APPOINTMENT PROGRESS TRACKING

BACKGROUND

Medical appointments are commonly associated with notoriously long wait times. According to numerous reviews from patients, the number one complaint is the wait time to see the doctor. For instance, online review sites allow patients to comment and provide corresponding star ratings for service providers. On these sites, low star ratings for physicians are often associated with comments citing long wait times. Often, reviewers complain of waiting from between thirty minutes to two hours. These reviews indicate that patient satisfaction with a physician's care can be heavily influenced by wait times, and that excessive wait times can lead to negative reviews of a physician's services.

Accordingly, improving the wait time for a patient can greatly improve the patient's satisfaction with the physician. In turn, this satisfaction will improve the patient's subjective feelings about their care, which can lead to more effective treatment and service. Specifically, when the patient is in a positive frame of mind at the beginning of the examination, the appointment naturally flows more smoothly. In addition, physicians often note that when they are behind schedule, they often spend time apologizing to the patient about being late, which reduces the amount of time available for actual patient care. By reducing or eliminating patient wait times, physicians can be more efficient and patients can have more positive experiences at appointments. Consequently, there is a need for improving patient wait times for medical appointments.

SUMMARY

Provided are various mechanisms and processes relating to medical appointment progress tracking.

In one aspect, which may include at least a portion of the subject matter of any of the preceding and/or following examples and aspects, the system includes a location sensor that tracks when a medical professional begins an examination of a patient by detecting when the medical professional logs into a computer to access the first patient's medical file. The system also includes a medical schedule processor that logs this time and compares this time with scheduling information to predict whether future appointments on that day will be delayed. The scheduling information is cryptographically separated from Health Insurance Portability and Accountability Act (HIPAA) information. The system further includes a notification interface that notifies upcoming patients if their appointments will be substantially delayed.

According to various examples, a process for notifying upcoming patients of schedule delays includes logging a time when a medical professional begins an appointment with a particular patient. This time is compared with scheduling information to determine whether future appointments in the schedule will be delayed. Based on this comparison and a prediction of delays for upcoming appointments, notifications are sent to upcoming patients if their appointments will be substantially delayed. Scheduling information is cryptographically separated from HIPAA information.

These and other embodiments are described further below with reference to the figures.

DETAILED DESCRIPTION OF EXAMPLE EMBODIMENTS

Figure 1:
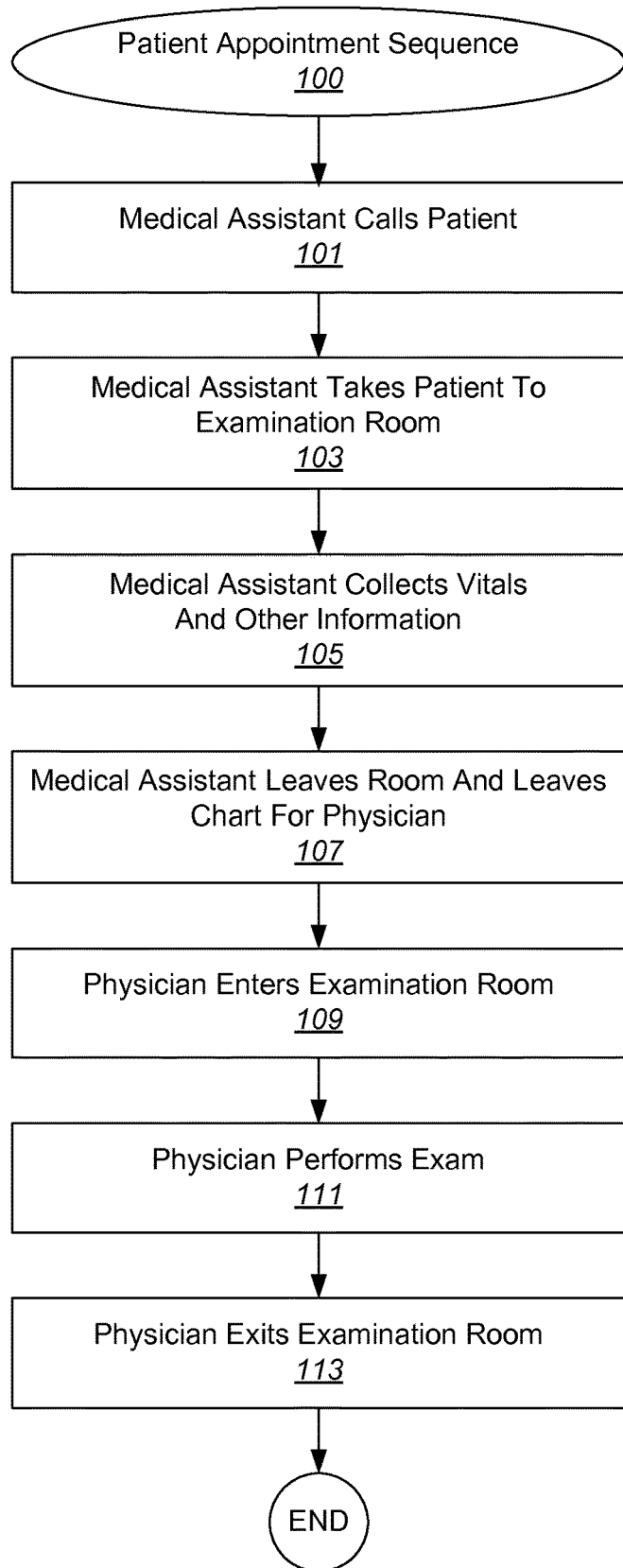
FIG. 1 is a flow chart illustrating one example of a patient appointment sequence.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

For example, the techniques of the present invention will be described in the context of particular scheduling mechanisms for medical offices. However, it should be noted that the techniques of the present invention apply to a wide variety of different scheduling mechanisms for a variety of different types of service entities such as dental offices, vision service providers, etc. In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors while remaining within the scope of the present invention unless otherwise noted. Furthermore, the techniques and mechanisms of the present invention will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Medical appointments are commonly associated with notoriously long wait times. Because patient satisfaction with a physician's care can be heavily influenced by wait times, excessive wait times can lead to negative reviews of a physician's services. By reducing or eliminating patient wait times, physicians can be more efficient and patients can have more positive experiences at medical offices.

Accordingly, various embodiments of the present invention address the issue of wait times in medical offices. In some examples, a physician's progress is monitored and any delays in the physician's schedule are detected. Patients are then informed of any delays or schedule changes in real-time. Specifically, a medical scheduling management system tracks the physician's progress and provides notifications, such as through text messages, to upcoming patients. These notifications can let patients know when a physician is running behind and ask them to arrive later than their originally scheduled appointment.

By notifying patients in real-time about schedule changes or fluctuations, the intent is to decrease the amount of time that each patient waits for their appointment to begin. In turn, reducing the wait time should increase patient satisfaction and result in more positive experiences with their physicians. Because reimbursement according to programs like Medicare will be highly dependent on patient satisfaction in the future, the amount physicians will be paid will be closely tied to their patients' satisfaction. By keeping patients informed of schedule status and changes, the system described in various examples of this disclosure has the potential to address one of the biggest problems with patient satisfaction: wait times. If patient satisfaction is increased, then there is a higher likelihood that physicians will be fully reimbursed for their work. In addition, higher patient satisfaction will also lead to more referrals from patients and more business for physicians.

According to various embodiments, physician activities, movements, and locations can be automatically or manually detected to allow improved appointment scheduling. For example, appointment start times can be manually or automatically triggered when a physician enters or a room and characteristics of the appointment can be used to determine whether later appointments need to be adjusted. In particular embodiments, mechanisms for tracking physician or other medical personnel activities, movements, and locations for scheduling appointments are firewalled from systems managing patient medical data. In some examples, different encryption mechanisms are used to encode patient medical data and medical personnel scheduling data so that access to one system does not permit access to another system. In other examples, different networks such as different virtual networks or different physical networks are used to transport the different types of data. According to various embodiments, patient medical data is encrypted during both storage and transmission using a different mechanism from medical personnel tracking data.

With reference to FIG. 1, shown is a flow chart illustrating one example of a patient appointment sequence. As shown, a typical patient appointment sequence 100 begins when a medical assistant (or nurse in some cases), calls a patient at 101 from the waiting room. Various embodiments will be described with reference to particular medical personnel. However, it should be noted that numerous activities can be performed by a variety of different medical professionals such as medical staff, medical assistants, nurses, physician assistants, physicians, residents, etc. A variety of triggers can also be used to initiate scheduling mechanisms, such as when a physician enters the patient's examination room, when a physician leaves the patient's examination room, when a nurse brings a patient to an examination room, etc.

According to various embodiments, a medical assistant then takes the patient to the examination room at 103. During the medical assistant's session with the patient, the medical assistant often collects information such as vitals and other data at 105. This may include aspects such as measuring temperature, blood pressure, and the like. In addition, this process can include weighing and measuring the height of the patient. In some cases, these measurements may be taken in a hallway on the way to the examination room. The medical assistant may also ask the patient questions and take notes. The medical assistant then leaves the examination room and leaves the patient's chart for the physician. The patient is then left alone in the examination room to wait for the physician. This time may also be used for changing into a gown, etc.

Next, the physician enters the examination room at 109. The physician performs the exam at 111, and then exits the examination room at 113. This concludes the process and the patient changes clothes, if appropriate, and collects their belongings before leaving the examination room.

As described, a medical appointment includes various phases that may include wait times. For instance, the patient may wait for a period of time before the medical assistant initially calls the patient at 101. The patient may also wait for a period of time between the time the medical assistant leaves the room at 107 and the time the physician enters the room at 109. Both of these wait times affect patient satisfaction and can lead to complaints relating to patient care. In addition, the amount of time that a physician spends with a particular patient, between blocks 109 and 113, affects whether future appointments that day will be on time or delayed. Accordingly, the timing of various phases of a patient appointment sequence can affect patient satisfaction and determine whether future appointments will be delayed.

Figure 2:
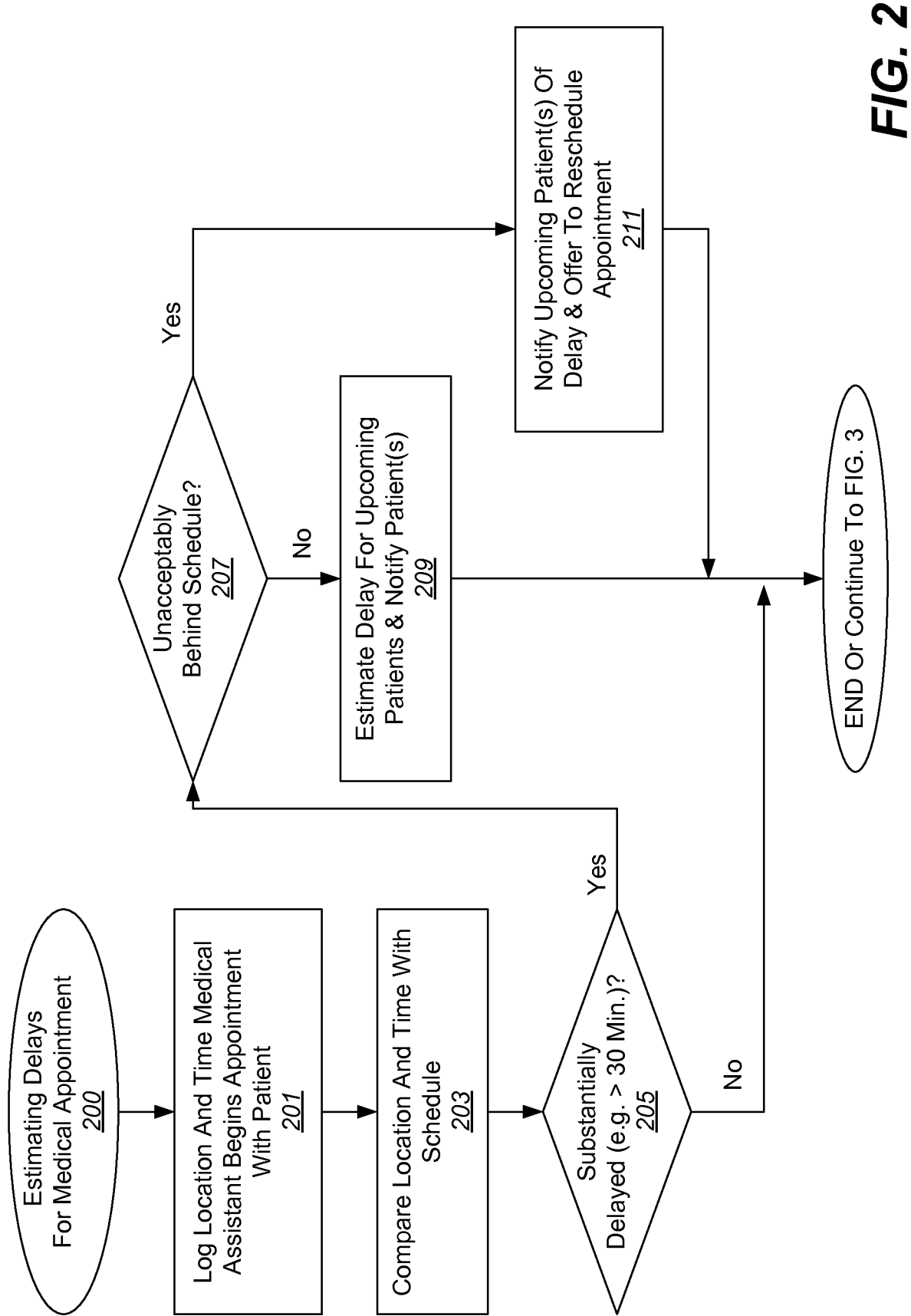
FIG. 2 is a flow sequence illustrating one example of a process for estimating delays for a medical appointment.
Figure 3:
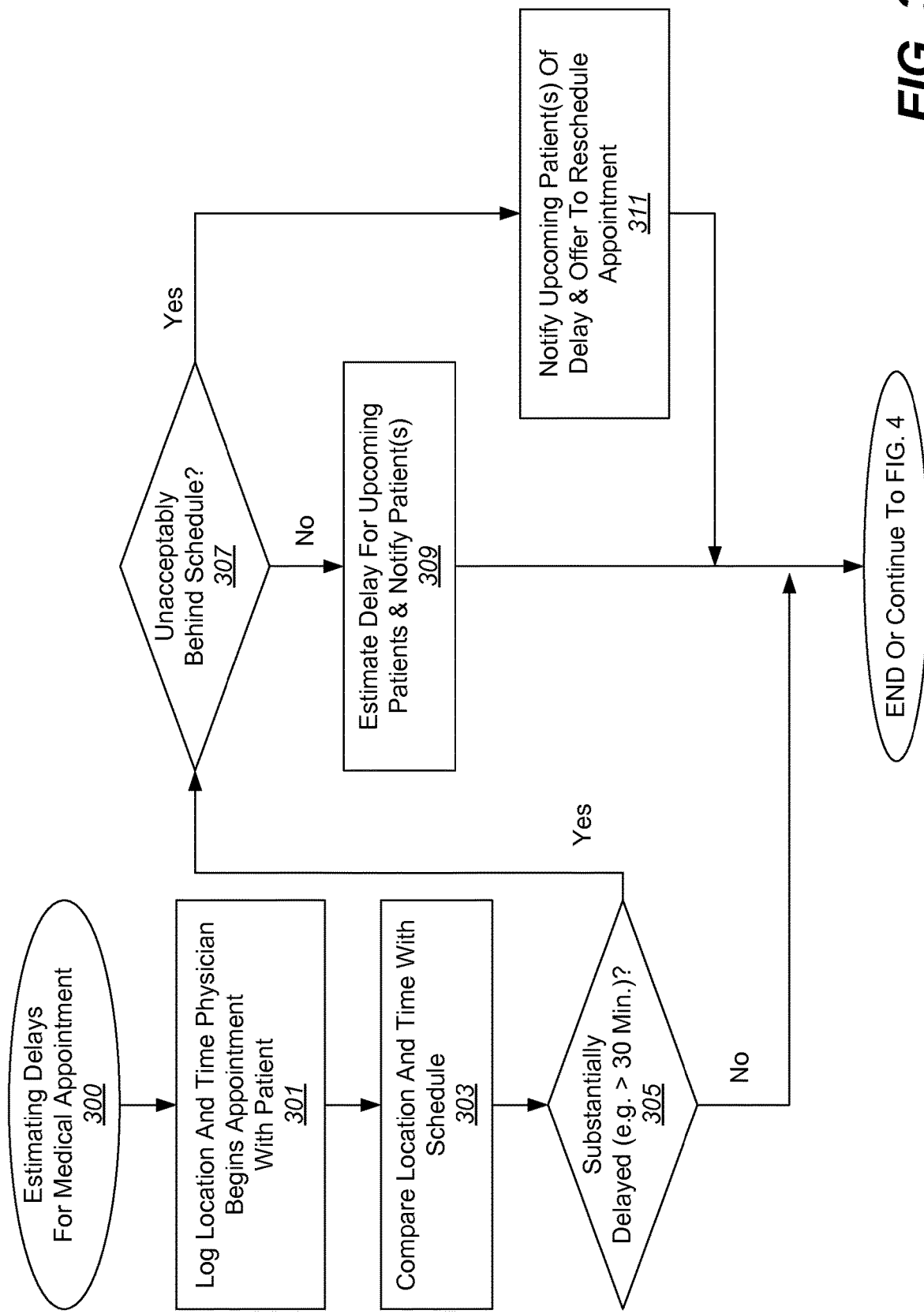
FIG. 3 is a flow sequence illustrating another example of a process for estimating delays for a medical appointment.
Figure 4:
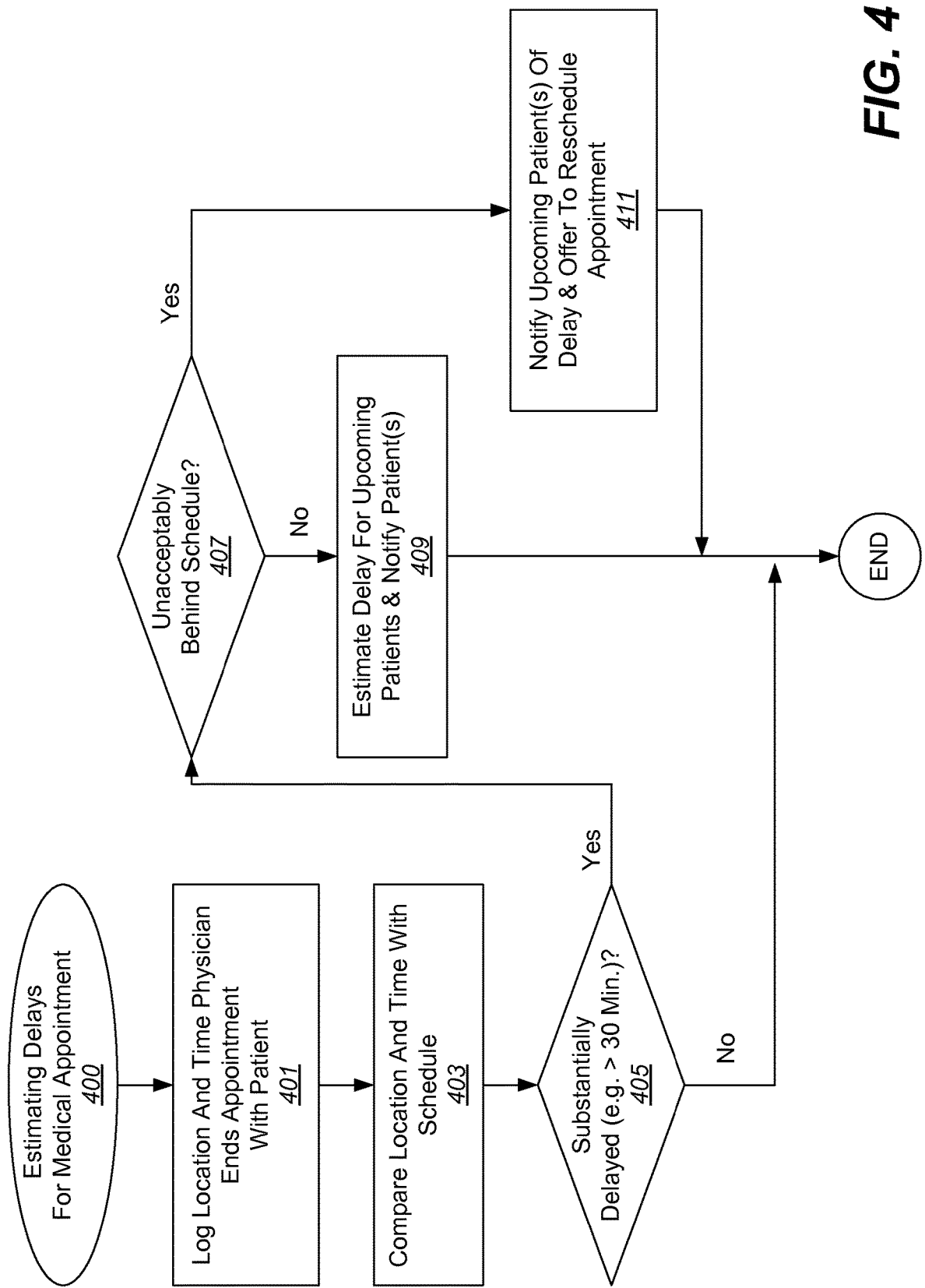
FIG. 4 is a flow sequence illustrating another example of a process for estimating delays for a medical appointment.

FIGS. 2-4 illustrate examples of flow sequences of processes for estimating delays for a medical appointment. The processes shown in each of the figures can be used alone or together, depending on the application. For instance, the process shown in FIG. 2 can be used alone in some examples, whereas, FIGS. 2-4 can be combined in other examples. In some aspects, the notification system can be viewed as a virtual waiting room. The system tracks when appointments are running late and the system informs an upcoming patient that their appointment is delayed and that they should delay arrival by a certain amount of time.

With reference to FIG. 2, shown is a flow sequence illustrating one example of a process for estimating delays for a medical appointment. In this example, delays in the schedule are estimated based on the time that a medical assistant (or nurse) begins an appointment with a patient. According to various embodiments, scheduling times, activity and location tracking, event monitoring, and other triggers pertinent to maintaining on-time scheduled appointments are referred to herein as scheduling information. In this process, estimating delays for a medical appointment 200 begins with logging a location and time when a medical assistant begins an appointment with a patient at 201. Next, this logged location and time is compared to a schedule at 203. This schedule includes the patients and times for their appointments for the current day. Based on this comparison, a determination is made whether the appointment is on time or substantially delayed at 205. For instance, if the time that the medical assistant begins the appointment is less than thirty (30) minutes later than the scheduled time for this patient, the appointment can be categorized as being on time and the process ends. If the time that the medical assistant begins the appointment is thirty (30) minutes or more past the scheduled time for this patient, then the appointment can be considered to be substantially delayed and the process continues at 207. Although thirty (30) minutes is used in this example to determine whether the appointment is on time, any amount of time can be used. In some examples, this amount of time can be set by a particular medical professional based on their preferences and office procedures.

In the present example, if the appointment is delayed thirty (30) or more minutes, a determination is then made whether the appointment is unacceptably behind schedule at 207. For the sake of this example, two (2) hours is used as a measure of when an appointment is unacceptably behind schedule. Appointments unacceptably behind schedule will not leave enough time for upcoming appointments, and consequently, will require that the upcoming appointments be rescheduled. Although two (2) hours delay is used as the threshold for determining when upcoming appointments need to be rescheduled, any amount of time can be used depending on the particular application of the system. For instance, certain physicians may want to decrease this time based on their allotted examination times or to generally increase patient satisfaction.

In the current example, if the delay is less than two (2) hours, then delays for upcoming appointments are then estimated and these upcoming patients are notified of these delays at 209. For these upcoming patients, the delay is between thirty (30) minutes and two (2) hours based on the current patient. In some examples, the delay can be propagated through the schedule equally. Specifically, if the current appointment is behind forty (40) minutes, then all of the upcoming appointments can be shifted forty (40) minutes later. However, in some examples, each subsequent appointment can be shifted a certain amount in addition to this forty (40) minutes if the system estimates that the physician will incur additional delays from the subsequent appointments. Once the delay is estimated for the upcoming patients, the patients are then notified.

According to various embodiments, upcoming patients are notified at 209 using their contact information. As described in more detail with regard to FIG. 5, this contact information can be stored in a database and accessed by the notification system. This contact information can be kept separate from patient medical records, in order to avoid any privacy concerns regarding the federal Health Insurance Portability and Accountability Act of 1996 (HIPAA). Specifically, the notification system accesses the contact information for upcoming patients, such as a phone number. In some examples, the notification system sends a text message to the upcoming patients notifying them of the expected delay and a later time that they should arrive. For instance, an upcoming patient originally scheduled for a two o'clock appointment may receive the following message: "Dear Jane, your appointment originally scheduled for 2:00 pm today with Dr. Smith is running behind schedule. Could you please arrive at 2:45 pm instead? Sorry for the delay. Thank you for your understanding." Alternatively, the notification system can send a voicemail or email to upcoming patients, depending on factors such as the patients' contact preferences and the office infrastructure. According to various embodiments, scheduling information such as medical professional location tracking, appointment start triggers, event monitoring, etc., are cryptographically separated from HIPAA information.

According to various embodiments, medical professional activities, movements, and locations can be automatically or manually detected to allow improved appointment scheduling. For example, appointment start times can be manually or automatically triggered when a physician enters or a room and characteristics of the appointment can be used to determine whether later appointments need to be adjusted. In one embodiment, an appointment start time is triggered when the medical professional logs into a computer to access the first patient's medical file, which may include vitals and notes for the examination.

In particular embodiments, mechanisms for tracking physician or other medical personnel activities, movements, and locations for scheduling appointments are firewalled from systems managing patient medical data. In some examples, different encryption mechanisms are used to encrypt HIPAA data and scheduling information so that access to one system does not permit access to another system. In other examples, different networks such as different virtual networks or different physical networks are used to transport the different types of data. According to various embodiments, patient medical data is encrypted during both storage and transmission using a different mechanism from medical personnel tracking data.

In the present example, if the delay is two (2) hours or more, then a determination is made whether some or all of the upcoming patients for the day need to be rescheduled. The patients that need rescheduling are then notified at 211 and are offered an opportunity to reschedule their appointments. For instance, if the physician is behind two hours, but can cancel two upcoming appointments and be back on schedule with subsequent patients, these two appointments may need to be rescheduled. In some cases, the schedule can be rearranged to cause as few reschedules as possible. In some examples, the option to reschedule can be offered through the text message, email, or voice message. For instance, an interactive sequence can be presented to the patient to allow them to reschedule immediately. This can provide convenience for both the patients and the front office. Specifically, in some examples, one or more alternative times can be offered to the patient and the patient can select one. Once the patient is notified according to the described process (or if no delay is found), the process either ends or continues as described in FIG. 3, depending on the desired application of the system.

With reference to FIG. 3, shown is a flow sequence illustrating another example of a process for estimating delays for a medical appointment. In this example, delays in the schedule are estimated based on the time that a physician begins an appointment with a patient. This process can be used alone in some examples, or it can continue following the process described above with regard to FIG. 2.

In the present example, estimating delays for a medical appointment 300 begins with logging a location and time when the physician begins an appointment with a patient at 301. Next, this logged location and time is compared to a schedule at 303. This schedule includes the patients and times for their appointments for the current day. Based on this comparison, a determination is made whether the appointment is on time or substantially delayed at 305. For instance, if the time that the physician begins the appointment is less than thirty (30) minutes later than the scheduled time for this patient, the appointment can be categorized as being on time and the process ends. If the time that the physician begins the appointment is thirty (30) minutes or more past the scheduled time for this patient, then the appointment can be considered to be substantially delayed and the process continues at 307. Although thirty (30) minutes is used in this example to determine whether the appointment is on time, any amount of time can be used. In some examples, this amount of time can be set by a particular medical professional based on their preferences and office procedures.

In the present example, if the appointment is delayed thirty (30) or more minutes, a determination is then made whether the appointment is unacceptably behind schedule at 307. For the sake of this example, two (2) hours is used as a measure of when an appointment is unacceptably behind schedule. Appointments unacceptably behind schedule will not leave enough time for upcoming appointments, and consequently, will require that the upcoming appointments be rescheduled. Although two (2) hours delay is used as the threshold for determining when upcoming appointments need to be rescheduled in the present example, any amount of time can be used depending on the particular application of the system. For instance, certain physicians may want to decrease this time based on their allotted examination times or to generally increase patient satisfaction.

In this example, if the delay is less than two (2) hours, then delays for upcoming appointments are then estimated and these upcoming patients are notified of these delays at 309. For these upcoming patients, the delay is between thirty (30) minutes and two (2) hours based on the current patient. In some examples, the delay can be propagated through the schedule equally. Specifically, if the current appointment is behind forty (40) minutes, then all of the upcoming appointments can be shifted forty (40) minutes later. However, in some examples, each subsequent appointment can be shifted a certain amount in addition to this forty (40) minutes if the system estimates that the physician will incur additional delays from the subsequent appointments. Once the delay is estimated for the upcoming patients, the patients are then notified. In some examples, if multiple factors are used to determine schedule delays, such as the time that the medical assistant begins the appointment and the time that the physician begins the appointment, then only one notification may be provided. For instance, a step can be included that determines whether a notification has already been sent to this patient, and if so, then an additional notification will not be sent. In other examples, updates to this notification with current waiting times and real-time appointment adjustments can be made as updated delays are predicted.

According to various embodiments, upcoming patients are notified at 309 using their contact information. As described in more detail with regard to FIG. 5, this contact information can be stored in a database and accessed by the notification system. This contact information can be kept separate from patient medical records, in order to avoid any privacy concerns regarding the federal Health Insurance Portability and Accountability Act of 1996 (HIPAA). Specifically, the notification system accesses the contact information for upcoming patients, such as a phone number. In some examples, the notification system sends a text message to the upcoming patients notifying them of the expected delay and a later time that they should arrive. For instance, a patient later in the day scheduled for a two o'clock appointment may receive the following message: "Dear Jane, your appointment originally scheduled for 2:00 pm today with Dr. Smith is running behind schedule. Could you please arrive at 2:45 pm instead? Sorry for the delay. Thank you for your understanding." Alternatively, the notification system can send a voicemail or email to upcoming patients, depending on factors such as the patients' contact preferences and the office infrastructure.

In the present example, if the delay is two (2) hours or more, then a determination is made whether some or all of the upcoming patients for the day need to be rescheduled.

The patients that need rescheduling are then notified at 311 and are offered an opportunity to reschedule their appointments. For instance, if the physician is behind two hours, but can cancel two upcoming appointments and be back on schedule with subsequent patients, these two appointments may need to be rescheduled. In some cases, the schedule can be rearranged to cause as few reschedules as possible. In some examples, the option to reschedule can be offered through the text message, email, or voice message. For instance, an interactive sequence can be presented to the patient to allow them to reschedule immediately. This can provide convenience for both the patients and the front office. Specifically, in some examples, one or more alternative times can be offered to the patient and the patient can select one. Once the patient is notified according to the process (or if no delay is found), the process either ends or continues as described in FIG. 4, depending on the desired application of the system.

In the present example, although both a location and time are logged when the physician begins the appointment, it should be noted that in some embodiments, the location need not be logged. For instance, if the patient and time are adequately identified and logged, then the location does not need to be logged in order to compare the actual appointment time with the scheduled appointment time. According to various examples, the location log can be used to determine when a physician is seeing a particular patient. Specifically, in cases where location logging is automated, such as with sensors, GPS, or the like, then the location can provide information about which patient a physician is currently seeing. In other cases, an appointment start time may be triggered when the medical professional logs into a computer to access the first patient's medical file, which may include vitals and notes for the examination. In these examples, logging a location is unnecessary because the appointment start time and current patient are collected at login.

With reference to FIG. 4, shown is a flow sequence illustrating another example of a process for estimating delays for a medical appointment. In this example, delays in the schedule are estimated based on the time that a physician ends an appointment with a patient. This process can be used alone in some examples, or it can continue following the process described above with regard to FIGS. 2 and/or 3.

In the present example, estimating delays for a medical appointment 400 begins with logging a location and time when the physician ends an appointment with a patient at 401. Next, this logged location and time is compared to a schedule at 403. This schedule includes the patients and times for their appointments for the current day. Based on this comparison, a determination is made whether the appointment is on time or substantially delayed at 405. For instance, if the time that the physician ends the appointment is less than thirty (30) minutes later than the scheduled time for this patient plus the allotted duration of this type of appointment, the appointment can be categorized as being on time and the process ends. If the time that the physician ends the appointment is thirty (30) minutes or more past the scheduled time for this patient plus the allotted duration of this type of appointment, then the appointment can be considered to be substantially delayed and the process continues at 407. Although thirty (30) minutes is used in this example to determine whether the appointment is on time, any amount of time can be used. In some examples, this amount of time can be set by a particular medical professional based on their preferences and office procedures.

In the present example, if the appointment is delayed thirty (30) or more minutes, a determination is then made whether the appointment is unacceptably behind schedule at 407. For the sake of this example, two (2) hours is used as a measure of when an appointment is unacceptably behind schedule. Appointments unacceptably behind schedule will not leave enough time for upcoming appointments, and consequently, will require that the upcoming appointments be rescheduled. Although two (2) hours delay is used as the threshold for determining when upcoming appointments need to be rescheduled in the present example, any amount of time can be used depending on the particular application of the system. For instance, certain physicians may want to decrease this time based on their allotted examination times or to generally increase patient satisfaction.

In this example, if the delay is less than two (2) hours, then delays for upcoming appointments are then estimated and these upcoming patients are notified of these delays at 409. For these upcoming patients, the delay is between thirty (30) minutes and two (2) hours based on the current patient. In some examples, the delay can be propagated through the schedule equally. Specifically, if the current appointment is behind forty (40) minutes, then all of the upcoming appointments can be shifted forty (40) minutes later. However, in some examples, each subsequent appointment can be shifted a certain amount in addition to this forty (40) minutes if the system estimates that the physician will incur additional delays from the subsequent appointments. Once the delay is estimated for the upcoming patients, the patients are then notified. In some examples, if multiple factors are used to determine schedule delays, such as the time that the medical assistant begins the appointment and/or the time that the physician begins the appointment, then only one notification may be provided. For instance, a step can be included that determines whether a notification has already been sent to this patient, and if so, then an additional notification will not be sent. In other examples, updates to this notification with current waiting times and real-time appointment adjustments can be made as updated delays are predicted.

According to various embodiments, upcoming patients are notified at 409 using their contact information. As described in more detail with regard to FIG. 5, this contact information can be stored in a database and accessed by the notification system. This contact information can be kept separate from patient medical records, in order to avoid any privacy concerns regarding the federal Health Insurance Portability and Accountability Act of 1996 (HIPAA). Specifically, the notification system accesses the contact information for upcoming patients, such as a phone number. In some examples, the notification system sends a text message to the upcoming patients notifying them of the expected delay and a later time that they should arrive. For instance, an upcoming patient scheduled for a two o'clock appointment may receive the following message: "Dear Jane, your appointment originally scheduled for 2:00 pm today with Dr. Smith is running behind schedule. Could you please arrive at 2:45 pm instead? Sorry for the delay. Thank you for your understanding." Alternatively, the notification system can send a voicemail or email to upcoming patients, depending on factors such as the patients' contact preferences and the office infrastructure.

In the present example, if the delay is two (2) hours or more, then a determination is made whether some or all of the upcoming patients for the day need to be rescheduled. The patients that need rescheduling are then notified at 411 and are offered an opportunity to reschedule their appointments. For instance, if the physician is behind two hours, but can cancel two upcoming appointments and be back on schedule with subsequent patients, these two appointments may need to be rescheduled. In some cases, the schedule can be rearranged to cause as few reschedules as possible. In some examples, the option to reschedule can be offered through the text message, email, or voice message. For instance, an interactive sequence can be presented to the patient to allow them to reschedule immediately. This can provide convenience for both the patients and the front office. Specifically, in some examples, one or more alternative times can be offered to the patient and the patient can select one. Once the patient is notified according to the process described (or if no delay is found), the process ends.

In the present example, although both a location and time are logged when the physician ends the appointment, it should be noted that in some embodiments, the location need not be logged. For instance, if the patient and time are adequately identified and logged, then the location does not need to be logged in order to compare the actual appointment time with the scheduled appointment time. According to various examples, the location log can be used to determine when a physician is seeing a particular patient. Specifically, in cases where location logging is automated, such as with sensors, GPS, or the like, then the location can provide information about which patient a physician is currently seeing. In other cases, an appointment end time is triggered when the medical professional closes or logs out of a patient's medical file on a computer. In these examples, logging a location is unnecessary because the appointment end time and current patient are collected when the medical professional logs off of the computer.

In some embodiments, multiple processes described with regard to FIGS. 2-4 can be used to provide feedback to the physician about schedule efficiencies or inefficiencies. For instance, data can be gathered and statistics can be generated for a particular day showing how many appointments were delayed, by how much, and whether the delays were caused by medical assistant delay, physician delay, or appointments that ran longer than the allotted time for the type of exam that was performed. In addition, statistics can be provided over periods of times, from days to months to years, depending on the time specified. In some examples, graphs and/or charts can be provided that show trends. Furthermore, suggestions can be provided based on the data provided, such as whether actual examination times are exceeding the allotted times, and by how much. Percentages can be provided showing how much overrun is occurring and how often. Suggestions such as extending the allotted times for examinations or spacing appointments further apart may be provided.

Figure 5:
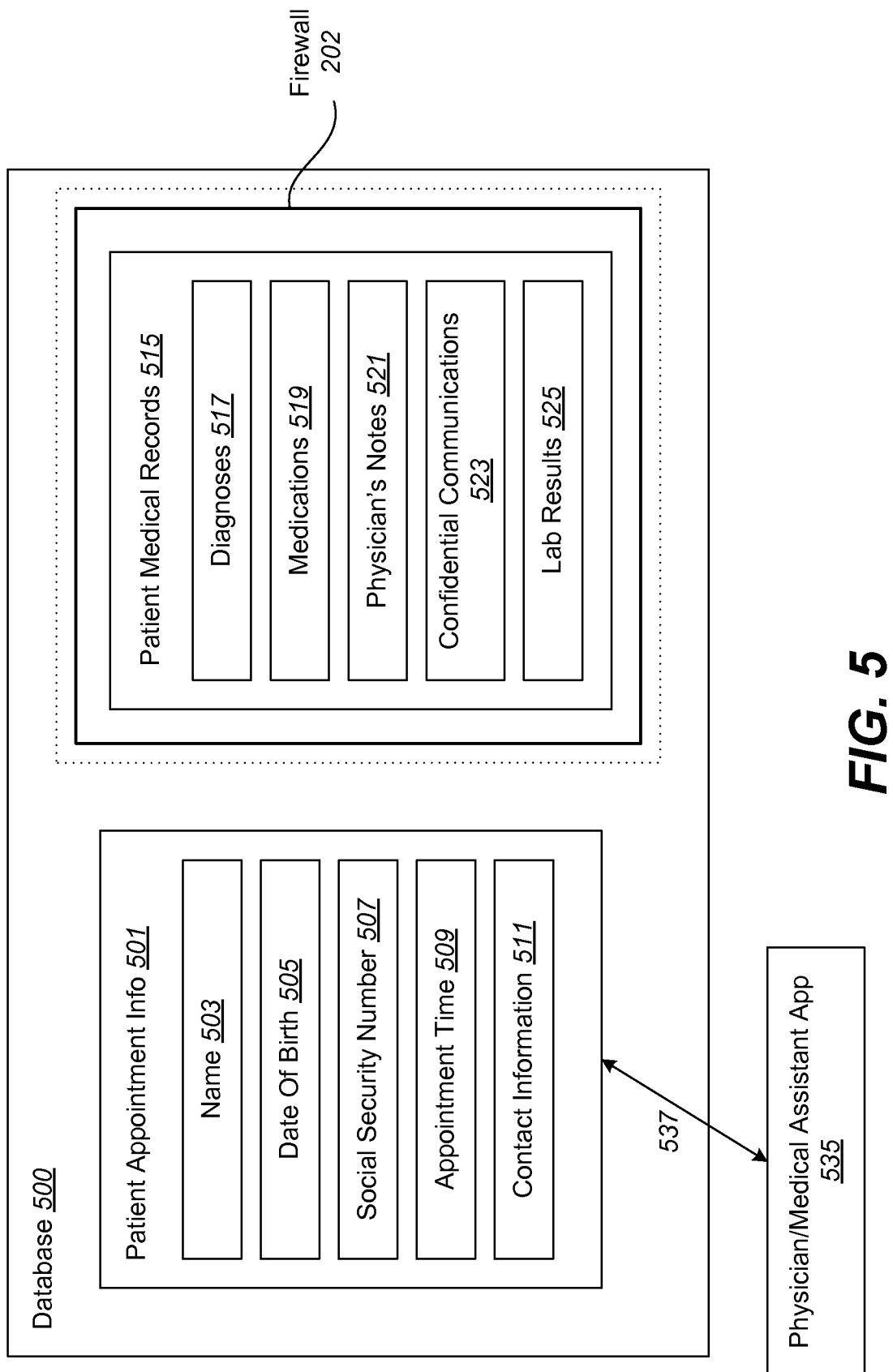
FIG. 5 is a diagrammatic representation of one example of a database designed to store patient information.

With reference to FIG. 5, shown is a diagrammatic representation of one example of a database designed to store patient information. As described above with regard to FIGS. 2-4, contact information for patients is retrieved by the notification system when upcoming patients are to be notified of a delay in their appointment times. However, in order to avoid any privacy concerns regarding HIPAA, the notification system is limited to retrieving contact information that is not related to patient-sensitive information.

In the present embodiment, database 500 includes patient appointment information 501 and patient medical records 515. Patient appointment information 501 includes information for numerous patients such as name 503, date of birth 505, social security number 507, appointment time(s) 509, and contact information 511. The contact information 511 can include information such as phone number(s) (for text and/or voicemail), email address, mailing address, and residence address. Additional or different information can be included, depending on the intended use of the database. However, patient appointment information is intended to include information that can be accessed by a scheduling or front office, without concerns about privacy under HIPAA.

In the present example, patient medical records 515 are protected by a firewall 202 that prevents inadvertent or unauthorized access to patient information protected under HIPAA. The patient medical records 515 include information for numerous patients such as diagnoses 517, medications 519, physician's notes 521, confidential communications 523, and lab results 525. Additional or different information can be included depending on the preferences of the physician or practice. The patient medical records 515 may include sensitive information that is protected under HIPAA privacy laws. Accordingly, this information must be handled carefully and access to it must be restricted to authorized people and systems.

According to various embodiments described herein, a medical scheduling management system notifies upcoming patients of a delay in their appointment times by accessing patient appointment information such as name 503, appointment time 509, and contact information 511. In some examples, the notification system is implemented as an app for mobile devices. This app 535 retrieves 537 patient appointment information to predict schedule delays, such as by retrieving appointment times 509 and comparing these appointment times 509 to real-time appointment progress for a particular physician. In addition, this app 535 retrieves contact information 511 and names 503 for patients that are to be notified of upcoming schedule delays. As indicated in the figure, the app 535 does not have access to patient medical records 515, and is prevented from accessing these patient medical records 515 by firewall 202. Although this example is described in the context of an app that can be implemented on one or more smartphones, mobile devices, etc., it should be recognized that this notification system can be implemented over any computer system. For instance, an office-based computer system can be updated manually by a medical assistant or other personnel to reflect current appointment times and the system can operate without any mobile devices.

Figure 6:
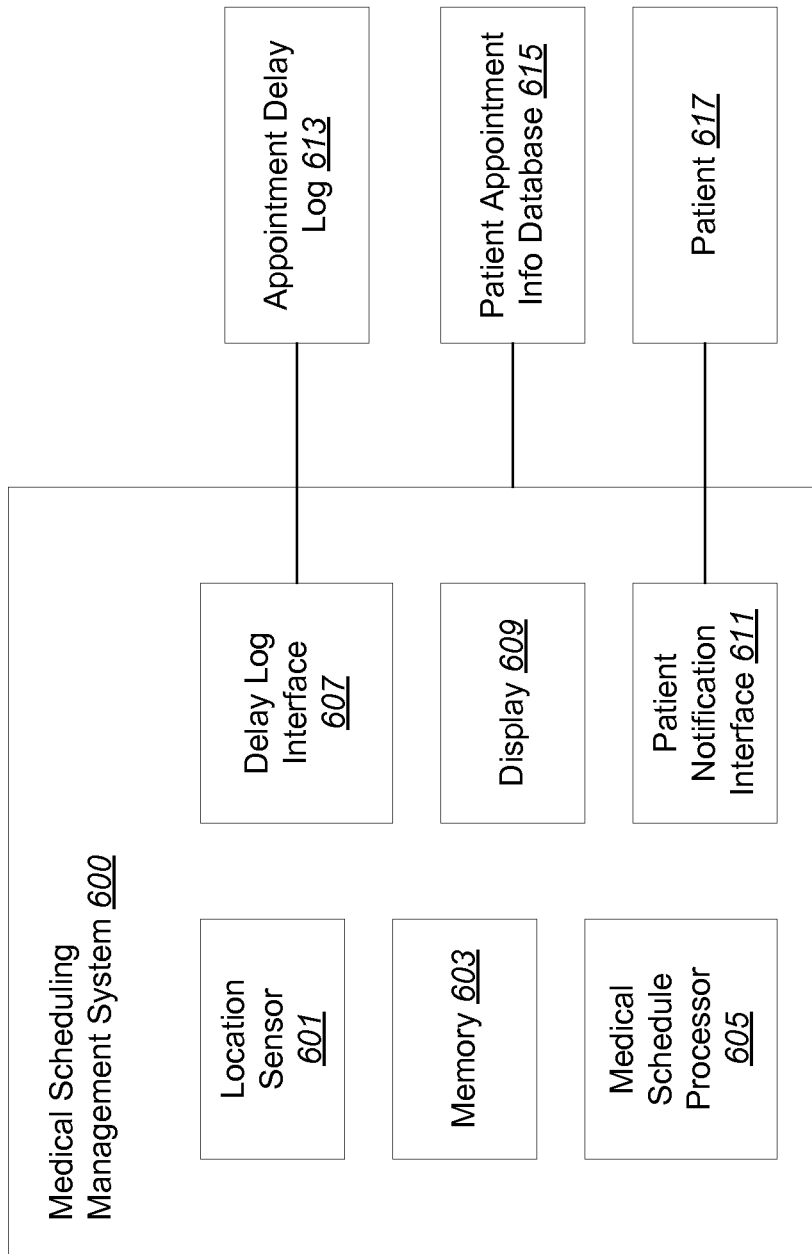
FIG. 6 is a diagrammatic representation of one example of a medical scheduling management system.
Figure 7:
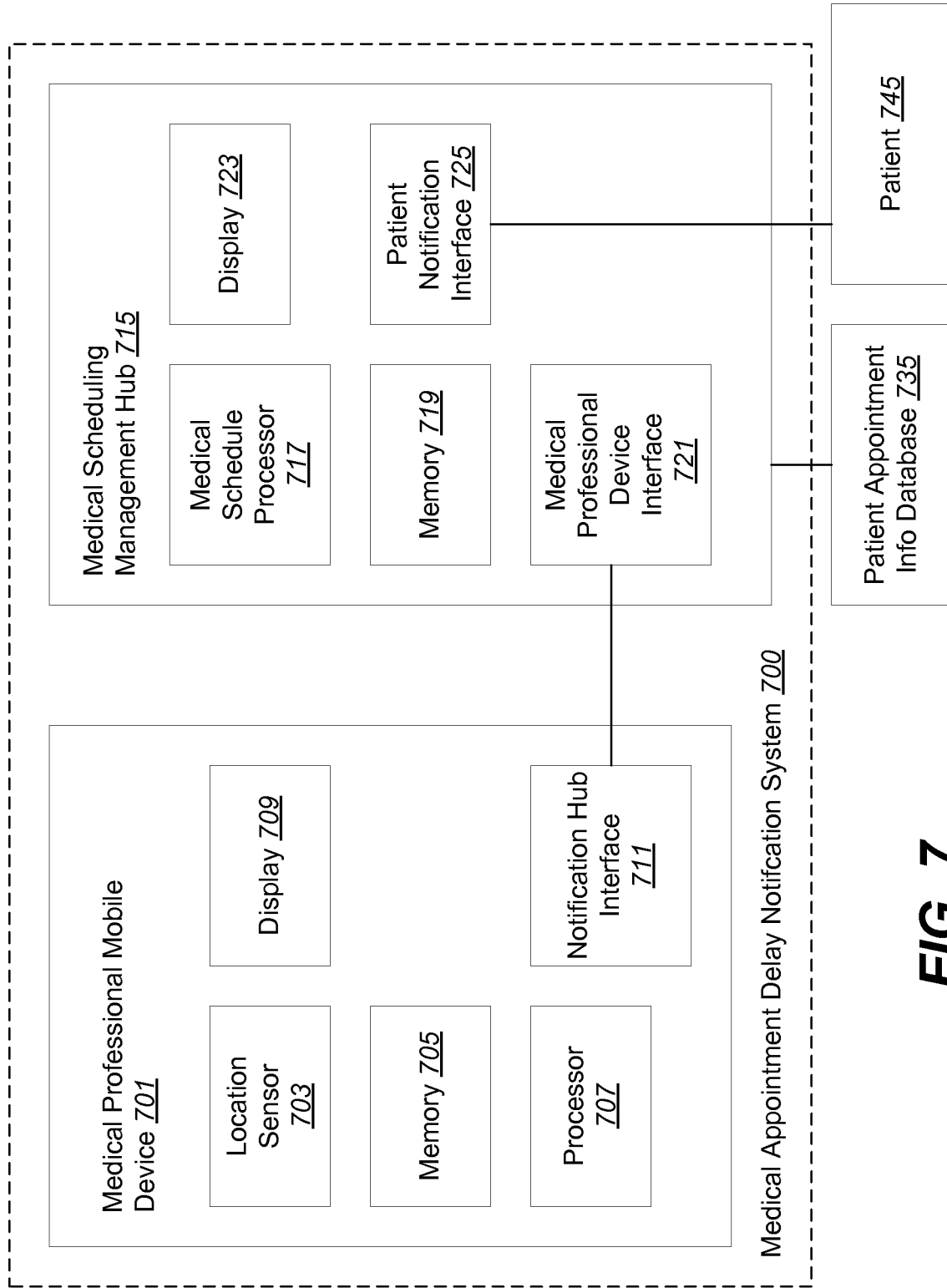
FIG. 7 is a diagrammatic representation another example of a medical scheduling management system.

As described in previous examples, a medical scheduling management system can be used to predict delays for upcoming appointments and notify upcoming patients of these delays. The medical scheduling management system can be implemented in various ways. FIGS. 6 and 7 illustrate two examples of configurations for medical scheduling management systems. It should be noted that although two particular examples are described, modifications and adjustments can be made within the scope of this disclosure.

With reference to FIG. 6, shown is a diagrammatic representation of one example of a medical scheduling management system. The medical scheduling management system 600 shown includes a location sensor 601, memory 603, medical schedule processor 605, delay log interface 607, display 609, and patient notification interface 611. The location sensor 601 is designed to detect when a medical professional enters an examination room to conduct an examination of a particular patient. This location sensor 601 can be implemented in numerous ways. In one example, a medical professional wears an identifier that is detectable in different areas of the office. The system is able to detect when the identifier, such as an RFID, etc. is in proximity to the location sensor. In some applications, there may be multiple location sensors in the system. In other examples, the location sensor 601 represents an input interface used by a medical assistant or other personnel to enter the location of the medical professional at a particular time. Specifically, location and time information can be entered manually into the system. In some instances, the location sensor 601 represents an input interface used by the medical professional to indicate when a particular appointment has started. Specifically, location and time information can be entered manually into the system. For instance, the next scheduled appointment may pop up or be otherwise selectable on a mobile device, and when the medical professional selects a button, the time is logged and this time is compared with the scheduled time. In yet other embodiments, the medical scheduling management system 600 can be implemented as an app on a mobile device, such as a smartphone. In these examples, the location sensor 601 can implement technologies such as GPS or other location sensing systems. In some examples, the location sensor 601 can be omitted, such as when only the patients and times are logged. In other examples, an appointment start time may be triggered when the medical professional logs into a computer to access the first patient's medical file, which may include vitals and notes for the examination. In these examples, logging a location is unnecessary because the appointment start time and current patient are collected at login. In some examples, the location sensor logs the start time of the appointment based on the medical professional's login.

In the present embodiment, the medical schedule processor 605 is designed to log the time when a medical professional enters an examination room for a particular appointment and compare this time with a schedule to predict whether future appointments in the schedule will be delayed. The schedule typically includes patients and times for appointments scheduled on a particular day. According to various examples, the schedule does not include any HIPAA information.

According to various embodiments, the medical schedule processor 605 is also designed to generate an efficiency report that includes statistics reflecting a number of appointments that were behind schedule and a number of appointments that overran their allotted durations for the selected time frame. Portions of the efficiency report are selectable and viewable in order to show details of particular appointments, such as the amounts that late appointments ran behind schedule and the amounts that appointments overran their allotted times. In addition, portions of the selected time frame are also viewable. In particular, the efficiency report includes customizable viewing that allows a certain type of appointment to be selected and viewed, where each of these certain types of appointment has the same allotted time. Depending on the preferences of the viewer, the efficiency report is viewable as a chart, graph, or other display format.

In some embodiments, the medical schedule processor 605 is further designed to make assessments based on the data. For instance, the medical schedule processor 605 may identify trends in the statistics, where the trends reflect patterns relating to when appointments tended to be behind schedule or overrun their allotted durations. These trends may be included in the efficiency report. In addition, the medical schedule processor 605 may provide suggestions for changes based on the trends in the statistics. In some examples, the medical schedule processor 605 identifies problematic appointments, such as those appointments that were significantly behind schedule or overran their allotted durations. In these examples, the efficiency report may include details of these problematic appointments.

In the present example, the memory 603 is used to store data and program instructions and maintain a local side cache. The program instructions may control the operation of an operating system and/or one or more applications, for example. In addition, display 609 is used to allow a user to interact with the system, such as through a monitor, screen, etc.

In the present embodiment, the notification interface 611 is used to notify upcoming patients if their appointments will be substantially delayed, as described in more detail with regard to FIGS. 2-4 above. This notification interface 611 is also designed to notify upcoming patients if their appointments need to be rescheduled. In some examples, the notification interface 611 is also designed to provide an option for these patients to reschedule their appointments. As described above, the notification interface 611 contacts a patient 617 using patient contact information such as a phone number, email, etc. In some examples, the notification interface 611 notifies a patient via a text message. In other examples, the notification interface 611 notifies a patient via a voicemail or email. Other notification modes can also be used, depending on the preferences of the patient and medical office.

In some embodiments, the notification interface 611 can be used to send data including current appointment status of the medical professional and predicted delays and modified appointment times for each appointment on the particular day to a medical scheduling management app that is viewable by patients of the medical professional. The current appointment status may include whether the current appointment is delayed and the amount of delay for the current appointment. According to various examples, predicted delays and modified appointment times are updated periodically. In some instances, the predicted delays and modified appointment times for a particular appointment are displayed in response to a user request. In other instances, the medical scheduling management app displays the current appointment status and predicted delays and modified appointment times for upcoming scheduled appointments. In some examples, the medical scheduling management app provides notifications to a user when additional delays or modified appointment times are detected. In addition, the medical scheduling management app may provide an option for a user to reschedule an upcoming appointment. Some implementations of the medical scheduling management app may provide an option to provide feedback related to patient satisfaction with a scheduled appointment after the scheduled appointment has ended. The feedback can include factors such as the level of satisfaction relating to whether the scheduled appointment was on time, the level of satisfaction relating to the duration of the appointment, and the level of satisfaction relating to receiving current appointment status and modified appointment times through the medical scheduling management app. Other factors may be substituted or added based on the practice.

In the present example, delay log interface 607 allows data such as real-time location and time information for appointments in-progress to be transmitted to an appointment delay log 613. This appointment delay log 613 is located in a separate location that may be accessed by other devices. For instance, if the medical scheduling management system 600 is implemented as an app on a mobile device, the appointment delay log 613 may include an office computer that is accessible to office staff and personnel. In other examples, the appointment delay log 613 can be located on a cloud drive. However, the delay log interface 607 and appointment delay log 613 can be omitted in some applications, depending on the needs of the practice.

As shown in the present embodiment, the medical scheduling management system 600 can interact with a patient appointment information database 615, such as the one shown and described with regard to FIG. 5. In particular, the medical scheduling management system 600 accesses the patient appointment information database 615 when predicting delays and when notifying upcoming patients, such as patient 617. As mentioned with regard to FIG. 5, the information accessible in the patient appointment information database 615 is not data that is protected under HIPAA.

With reference to FIG. 7, shown is a diagrammatic representation of another example of a medical scheduling management system. In this example, the medical scheduling management system 700 includes a medical scheduling management hub 715 and one or more medical professional mobile devices 701. The medical professional mobile device 701 can be implemented as a mobile device, such as a smart phone, tablet, etc. In other examples, this mobile device 701 can be implemented as a wearable device such as a bracelet, fob, charm, clip, etc. As shown, the medical scheduling management hub 715 is implemented on a computer such as a mobile device, office computer, server, etc. This serves as a "home base" for the system. In some examples, this hub 715 is implemented on a central office computer or on the cloud.

In the present example, the medical professional mobile device 701 includes a location sensor 703, memory 705, processor 707, display 709, and notification hub interface 711. The location sensor 703 is designed to detect when a medical professional enters an examination room to conduct an examination of a particular patient. This location sensor 703 can be implemented in numerous ways. In one example, the location sensor is able to identify when the medical professional is in different areas of the office. In these examples, the location sensor 703 can implement technologies such as GPS, RFID, Bluetooth, triangulation mechanisms, cameras, or other location sensing systems. In other examples, the location sensor 703 represents an input interface used by the medical professional to indicate when a particular appointment has started. Specifically, location and time information can be entered manually into the system. For instance, the next scheduled appointment may pop up or be otherwise selectable the mobile device 701, and when the medical professional selects a button, the time is logged and this time is compared with the scheduled time. In some embodiments, the location sensor 703 can be omitted, such as when only patient and time information are logged. In other examples, an appointment start time may be triggered when the medical professional logs into a computer to access the first patient's medical file, which may include vitals and notes for the examination. In these examples, logging a location is unnecessary because the appointment start time and current patient are collected at login. In some examples, the location sensor logs the start time of the appointment based on the medical professional's login.

In the present example, the medical professional mobile device 701 includes memory 705, which is used to store data and program instructions and maintain a local side cache. The program instructions may control the operation of an operating system and/or one or more applications, for example. In some examples, the size of the memory 705 may be limited, as when most of the processing and storage of data is performed at the medical scheduling management hub 715. In addition, the processor 707 may include limited processing of the data collected. For instance, the data collected may include the times and locations of particular appointments, and the processor can be used to format the information before sending it to the medical scheduling management hub 715. The limited memory 705 and processor 707 sizes and capabilities may be appropriate especially in cases when the medical professional mobile device 701 is implemented as a wearable because the components can be smaller and more conveniently designed into a smaller casing to be comfortably worn. In the present example, display 709 is used to allow the medical professional to interact with the system, such as through a screen, touch screen, etc. As described above, the medical professional may input data through this display 709 and/or view options through the display.

In the present example, the medical professional mobile device 701 also includes a notification hub interface 711. This notification hub interface 711 is used to communicate with the medical scheduling management hub 715. In particular, data regarding real-time appointment start times are sent via the notification hub interface 711 to the medical scheduling management hub 715 via medical professional device interface 721. In some examples, the medical professional device interface 721 is used to send messages to the medical professional mobile device 701 via the notification hub interface 711, such as "Has the Smith 1:10 pm appointment begun?"

In the present embodiment, the medical scheduling management hub includes a medical schedule processor 717 designed to log the time when a medical professional enters an examination room for a particular appointment and compare this time with a schedule to predict whether future appointments in the schedule will be delayed. The schedule typically includes patients and times for appointments scheduled on a particular day. According to various examples, the schedule does not include any HIPAA information.

According to various embodiments, the medical schedule processor 717 is also designed to generate an efficiency report that includes statistics reflecting a number of appointments that were behind schedule and a number of appointments that overran their allotted durations for the selected time frame. Portions of the efficiency report are selectable and viewable in order to show details of particular appointments, such as the amounts that late appointments ran behind schedule and the amounts that appointments overran their allotted times. In addition, portions of the selected time frame are also viewable. In particular, the efficiency report includes customizable viewing that allows a certain type of appointment to be selected and viewed, where each of these certain types of appointment has the same allotted time. Depending on the preferences of the viewer, the efficiency report is viewable as a chart, graph, or other display format.

In some embodiments, the medical schedule processor 717 is further designed to make assessments based on the data. For instance, the medical schedule processor 717 may identify trends in the statistics, where the trends reflect patterns relating to when appointments tended to be behind schedule or overrun their allotted durations. These trends may be included in the efficiency report. In addition, the medical schedule processor 717 may provide suggestions for changes based on the trends in the statistics. In some examples, the medical schedule processor 717 identifies problematic appointments, such as those appointments that were significantly behind schedule or overran their allotted durations. In these examples, the efficiency report may include details of these problematic appointments.

In the present example, the memory 719 is used to store data and program instructions and maintain a local side cache. The program instructions may control the operation of an operating system and/or one or more applications, for example. In addition, display 723 is used to allow a user to interact with the system, such as through a monitor, screen, etc.

In the present embodiment, the patient notification interface 725 is used to notify upcoming patients if their appointments will be substantially delayed, as described in more detail with regard to FIGS. 2-4 above. This notification interface 725 is also designed to notify upcoming patients if their appointments need to be rescheduled. In some examples, the notification interface 725 is also designed to provide an option for these patients to reschedule their appointments. As described above, the notification interface 725 contacts a patient 745 using patient contact information such as a phone number, email, etc. In some examples, the notification interface 725 notifies a patient via a text message. In other examples, the notification interface 725 notifies a patient via a voicemail or email. Other notification modes can also be used, depending on the preferences of the patient and medical office.

In some embodiments, the notification interface 725 can be used to send data including current appointment status of the medical professional and predicted delays and modified appointment times for each appointment on the particular day to a medical scheduling management app that is viewable by patients of the medical professional. The current appointment status may include whether the current appointment is delayed and the amount of delay for the current appointment. According to various examples, predicted delays and modified appointment times are updated periodically. In some instances, the predicted delays and modified appointment times for a particular appointment are displayed in response to a user request. In other instances, the medical scheduling management app displays the current appointment status and predicted delays and modified appointment times for upcoming scheduled appointments. In some examples, the medical scheduling management app provides notifications to a user when additional delays or modified appointment times are detected. In addition, the medical scheduling management app may provide an option for a user to reschedule an upcoming appointment. Some implementations of the medical scheduling management app may provide an option to provide feedback related to patient satisfaction with a scheduled appointment after the scheduled appointment has ended. The feedback can include factors such as the level of satisfaction relating to whether the scheduled appointment was on time, the level of satisfaction relating to the duration of the appointment, and the level of satisfaction relating to receiving current appointment status and modified appointment times through the medical scheduling management app. Other factors may be substituted or added based on the practice.

As shown in the present embodiment, the medical scheduling management hub 715 interacts with a patient appointment information database 735, such as the one shown and described with regard to FIG. 5. In particular, the medical scheduling management hub 715 accesses the patient appointment information database 735 when predicting delays and when notifying upcoming patients, such as patient 745. As mentioned with regard to FIG. 5, the information accessible in the patient appointment information database 735 is not data that is protected under HIPAA.

Although FIGS. 6 and 7 describe particular configurations of medical scheduling management systems, it should be recognized that various configurations can be constructed within the scope of this disclosure. In addition, the system can be used to provide feedback to the physician and/or practice to allow them to generate physician/examination efficiency reports in some examples. For instance, the system can generate reports indicating the percentage of appointments that were delayed and by how much they were delayed. In some cases, the reports can be customizable to indicate factors such as whether certain types of appointments are delayed more often, times of day when more appointments are delayed, days of the week or month when appointments are delayed more often, etc. This feedback can be used by the physician to improve their care and service and become more efficient in their practice. This can lead to more satisfied patients, a more pleasant experience for the patients and medical professionals, and a higher rate of return for the physician and practice.

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present embodiments are to be considered as illustrative and not restrictive.

What is claimed is:

1. A medical scheduling management system comprising:
    a display located within an examination room, wherein the display is configured to provide an input interface;
    a location sensor located within the examination room, wherein the location sensor is configured to form a connection with an identification device worn by a medical professional when the identification device is within a proximity to the location sensor,
       wherein the medical scheduling management system is configured to record a first appointment start time when the medical professional logs in via the input interface during the connection formed between the location sensor and the identification device to access a medical file of a first patient,
       wherein the medical file includes vitals and notes corresponding to the first patient, and
       wherein the first appointment start time indicates when the medical professional begins a first appointment with the first patient;
    a medical schedule processor configured to:
       receive the first appointment start time, and
       compare the first appointment start time with scheduling information to determine whether future appointments will be substantially delayed, wherein the scheduling information includes a plurality of scheduled appointments with different patients on a particular day, wherein the plurality of scheduled appointments includes the first appointment for the first patient and a second appointment for a second patient,
       wherein the scheduling information is cryptographically separated from Health Insurance Portability and Accountability Act (HIPAA) information, and wherein HIPAA information is encrypted for storage and transmission using a first mechanism distinct from a second mechanism used to store and transmit the scheduling information; and
    a notification interface configured to transmit a notification message to a user device corresponding to the second patient if the second appointment will be substantially delayed.

2. The medical scheduling management system of claim 1, wherein the notification interface is further configured to notify the second patient if the second appointment needs to be rescheduled, and wherein the notification interface is further configured to provide an option for the second patient to reschedule the second appointment.

3. The medical scheduling management system of claim 1, wherein at least one appointment is scheduled between the first appointment and the second appointment.

4. The medical scheduling management system of claim 1, wherein the notification interface is configured to notify the second patient via text message.

5. The medical scheduling management system of claim 1, wherein the medical professional is a physician.

6. The medical scheduling management system of claim 1, wherein the medical professional is a medical assistant or nurse.

7. A method comprising:
    forming a connection between a location sensor of a medical scheduling management system and an identification device that is within a proximity to the location sensor, wherein the identification device is worn by a medical professional, wherein the location sensor is located within an examination room;
    receiving login information from the medical professional to access a medical file of a first patient, the medical file including vitals and notes corresponding to the first patient, wherein the login information is received via an input interface during the connection formed between the location sensor and the identification device, wherein the input interface is provided by a display of the medical scheduling management system, wherein the display is located within the examination room;
    recording a first appointment start time upon receiving the login information during the connection formed between the location sensor and the identification device, the first appointment start time indicating when the medical professional begins a first appointment with the first patient; and
    comparing the first appointment start time with scheduling information to determine whether future appointments will be delayed, wherein the scheduling information includes a plurality of scheduled appointments with different patients on a particular day, wherein the plurality of scheduled appointments includes the first appointment for the first patient and a second appointment for a second patient, wherein the scheduling information is cryptographically separated from Health Insurance Portability and Accountability Act (HIPAA) information, and wherein HIPAA information is encrypted for storage and transmission using a first mechanism distinct from a second mechanism used to store and transmit scheduling information;
    determining whether the second appointment will be substantially delayed based on whether the future appointments will be delayed; and
    transmitting notification message, via a notification interface of the medical scheduling management system, to a user device corresponding to the second patient if the second appointment will be substantially delayed.

8. The method of claim 7, wherein determining whether the second appointment will be substantially delayed includes comparing a predicted start time associated with the second appointment with an originally scheduled time for the second appointment, wherein the predicted start time is predicted based on an amount of delay from the first appointment.

9. The method of claim 8, wherein determining whether the second appointment will be substantially delayed includes predicting that the predicted start time will be more than thirty (30) minutes later than the originally scheduled time for the second appointment.

10. The method of claim 7, wherein additional appointments are scheduled between the first appointment and the second appointment.

11. The method of claim 8, further comprising determining whether the second appointment needs to be rescheduled.

12. The method of claim 11, wherein determining whether the second appointment needs to be rescheduled includes determining whether the predicted start time is more than two (2) hours later than an originally scheduled time for the second appointment.

13. The method of claim 12, further comprising notifying the second patient that the second appointment needs to be rescheduled if the predicted start time is more than two (2) hours later than the originally scheduled time for the second appointment.

14. The method of claim 13, further comprising providing an option for the second patient to reschedule the second appointment.

15. The method of claim 7, wherein transmitting the notification message includes sending a text message to the user device.

16. The method of claim 7, wherein transmitting the notification message includes sending a voice message to the user device.

17. The method of claim 7, wherein the medical professional is a medical assistant or nurse.

18. The method of claim 7, wherein the medical professional is a physician.

19. The method of claim 7, wherein transmitting the notification message includes retrieving contact information associated with the second patient, wherein the contact information is stored separately from patient medical records subject to HIPAA regulations.

20. The method of claim 7, wherein the medical file of the first patient includes HIPAA information, wherein HIPAA information is protected from inadvertent or unauthorized access by a network firewall.

* * * * *